United States Patent [19]

Koosen

[11] Patent Number: 5,091,696

[45] Date of Patent: Feb. 25, 1992

[54] METALLIC COATING MEASURING METHOD AND APPARATUS

[76] Inventor: Peter P. Roosen, 3560 Allsop Road, Nanaimo, British Columbia, Canada, V9R 5K3

[21] Appl. No.: 561,617

[22] Filed: Aug. 2, 1990

[30] Foreign Application Priority Data

Aug. 9, 1989 [CA] Canada .................................. 607963

[51] Int. Cl.⁵ .......................... G01B 7/10; G01R 33/12
[52] U.S. Cl. .................................................... 324/229
[58] Field of Search ............... 324/228, 229, 230, 231, 324/236

[56] References Cited

U.S. PATENT DOCUMENTS

| | | | |
|---|---|---|---|
| 4,255,709 | 3/1981 | Zatsepin et al. | 324/229 |
| 4,593,244 | 6/1986 | Summers et al. | 324/230 |
| 4,673,877 | 6/1987 | Sakamoto et al. | 324/230 X |
| 4,752,739 | 6/1988 | Wang | 324/230 |
| 4,763,071 | 8/1988 | McGee et al. | 324/229 X |
| 4,843,319 | 6/1986 | Lara | 324/229 X |
| 4,843,320 | 6/1989 | Spies | 324/229 X |

Primary Examiner—Kenneth A. Wieder
Assistant Examiner—W. S. Edmunds
Attorney, Agent, or Firm—John Russell Uren

[57] ABSTRACT

A metallic material measuring method and apparatus. The material is positioned within a coil and a high frequency alternating current is applied to the coil. The change in inductive resistance in the coil from a reference state to a state where the material to be measured is positioned within the coil allows a determination of the properties of the metallic materials to be made.

10 Claims, 7 Drawing Sheets

METALLIC COATING MEASURING METHOD AND APPARATUS

INTRODUCTION

This invention relates to nondestructive testing of metallic materials and, in particular, to the measurement of properties of such materials using the application of a high frequency alternating current to a coil and measuring the change in inductive resistance of the coil.

BACKGROUND OF THE INVENTION

It is desirable to measure the physical and chemical properties of metallic materials in order to ensure that such materials meet specifications to which they have been designed. In galvanizing steel wire, for example, it is desirable to ensure that the amount of the galvanizing material used to coat the wire is correct both for economic and operating reasons.

Galvanizing a wire comprises pulling the annealed and acid pickled wire through a bath of molten zinc and drawing the wire upward through a wiper to remove the excess zinc coating. To change the amount of coating, one can vary the speed at which the wire is drawn through the bath or the amount of wiping.

The measurement of the zinc coating is accomplished by removing samples of wire from the beginning and the end of the wire which was coated. The samples are then submitted to "gravimetric testing" wherein they are initially weighed and subsequently immersed in hydrochloric acid to remove the zinc coating. The samples are again weighed to determine the difference and, hence, the weight of the coating. Such results, while determining with some accuracy the weight of the zinc on the sample pieces, are slowly obtained and the sample pieces are only indicative of the amount of coating on the wire as a whole. Furthermore, it is a relatively expensive process.

Other techniques have also been used to measure coatings. One such technique is disclosed in U.S. Pat. No. 4,593,244 to Summers et al. This technique uses the so called "skin effect" to measure the amount of coating on a substrate. The aforementioned skin effect is so named because when a frequency is applied to a metallic substance, the magnetic flux is principally restricted to the outer portion of the body and a less permeable coating is more deeply penetrated than a more permeable substrate. Thus, if an oscillator driven sensor coil has a coated substrate positioned within the coil, the impedance will be different from its value when an uncoated substrate is placed within the coil. The use of the coating "hides" the substrate since the coating will affect the coil's impedance more than the substrate. Thus, the characteristics of the coating are indicated by the change in coil impedance which is readily measured.

In such a process, the oscillator frequency applied to the coil is important to the sensitivity of the instrument. While it is believed the explanations given throughout this application correctly explain the phenomena, such explanations are given in the interest of full and complete disclosure and applicant would not wish to be bound by the explanations if, subsequently, the explanations are found to be incorrect or partially so or if further explanations more accurately define the phenomena which are not presently known to the applicant.

There are two competing frequency dependant parameters to consider as follows:

$$\delta_{SKIN\ DEPTH} \propto \left[\frac{1}{f}\right]^{\frac{1}{2}} \quad (1)$$

$$E_{COIL\ \&\ SAMPLE\ CORE} \propto [f]^{\frac{1}{2}} ; 7\ \text{kHz} < f < 5\ \text{MHz} \quad (2)$$

As given above in (1), the first parameter that governs impedance sensitivity is the skin depth. The skin depth measured varies with the reciprocal of the square root of the frequency. Thus, in terms of skin depth criteria, the ideal applied frequency would produce a skin depth as deep as the coating at its thickest point. If a shallower skin depth were chosen, the instrument would "miss" part of the coating so that, essentially, the skin depth sets an upper limit on measurable coating thickness. If a deeper skin depth were chosen, an unnecessary amount of the substrate would be "seen" by the instrument and the coating measurement would become overshadowed by the spurious effects of the substrate. Thus, the skin depth criterion affects sensitivity in two ways. First, it sets the maximum measurable coating thickness and, second, it determines the amount of overshadowing from the substrate.

As given above in (2), the second parameter that governs sensitivity is the extent to which the coil resistance varies with the amount of the inserted sample coating. A large variation in resistance is easy to measure and leads to a sensitive instrument. The resistance of the coil and sample core combination increases with the square root of frequency. At least to the frequency upper limit of relation (2), increasing frequency increases the spread of the resistances produced by sample cores with varying amounts of coating. Thus, the resistance criterion also affects sensitivity in two ways. First, it sets the minimum measurable amount of coating and, second, it sets the minimum measurable change in amount of coating.

There is, in addition, a further important factor in the measurement system, namely the resonant frequency of the sensor coil and associated capacitance. Signals are strongest at resonance and thus for greatest sensitivity, a coil and capacitance should be used which has a resonant frequency at the oscillator frequency that was chosen by utilizing the criteria of relations (1) and (2).

The principle shortcomings of the previous attempts have been the complexity of the circuitry required and the imprecision of results stemming from insensitivity. Thus, only a fairly limited range of sample sizes could be measured. All three problems have arisen from the choice of either the applied or the resonant frequency, the frequencies chosen erring on the low side.

In one previous technique attributable to the present inventor in his undergraduate thesis entitled "Continuous On-line Electronic Zinc Coating Weight Measurement System for Galvanized Steel Wire" filed at Lakehead University on Apr. 28, 1988, a lower applied frequency was used than the resonance of the sensor coil and associated capacitance. Since the signal strength was also lower than necessary, changes in the resistance of the coil were difficult to measure and the implementation instrumentation was relatively insensitive. In choosing the applied frequency, the relationship set out in relation (2) was then not apparent. As a result, a lower frequency was used with the concomitant problems set out above.

In a further previous technique as disclosed in aforementioned Summers et al. reference, a skin depth margin of error was included. A low enough frequency was used to ensure that the skin depth was two to four times the predicted maximum coating thickness. This tradeoff resulted in dramatically compressing the coil resistance spread predicted by relation (2). This lead to unnecessarily complicated bridge and amplification circuitry. The result was that only coarse measurements could be made since small changes in the amount of coating did not vary the resistance of the sensor by a sufficiently measurable amount.

SUMMARY OF THE INVENTION

According to one aspect of the invention, there is disclosed a method of measuring the coating on a coated substrate comprising the steps of applying a high A.C. frequency to a coil, said high A.C. frequency being approximately the same as the resonant frequency of said coil and associated capacitance, inserting said coated substrate into coil and measuring the impedance change of said coil upon insertion of said coated substrate.

According to a further aspect of the invention, there is disclosed an apparatus for measuring the coating of a coated substrate comprising coil means and associated capacitance having a resonant frequency, high A.C. frequency generating means operable to apply a high A.C. frequency having a value approximately equal to the value of said resonant frequency of said coil means and associated capacitance and impedance change measuring means operable to measure the change in impedance of said coil means.

According to yet a further aspect of the invention, there is disclosed a method of measuring the change in impedance of a coil means comprising measuring the impedance of said coil means, bringing a metallic material into the proximity of a coil means, applying a high A.C. frequency to said coil means at approximately the resonant frequency of said coil means and associated capacitance and measuring the change in impedance of said coil means with said metallic material in proximity of said coil means.

BRIEF DESCRIPTION OF THE SEVERAL VIEWS OF THE DRAWINGS

An embodiment of the invention will now be described, by way of example only, with the use of drawings in which.

DESCRIPTION OF SPECIFIC EMBODIMENT

Figure 1:
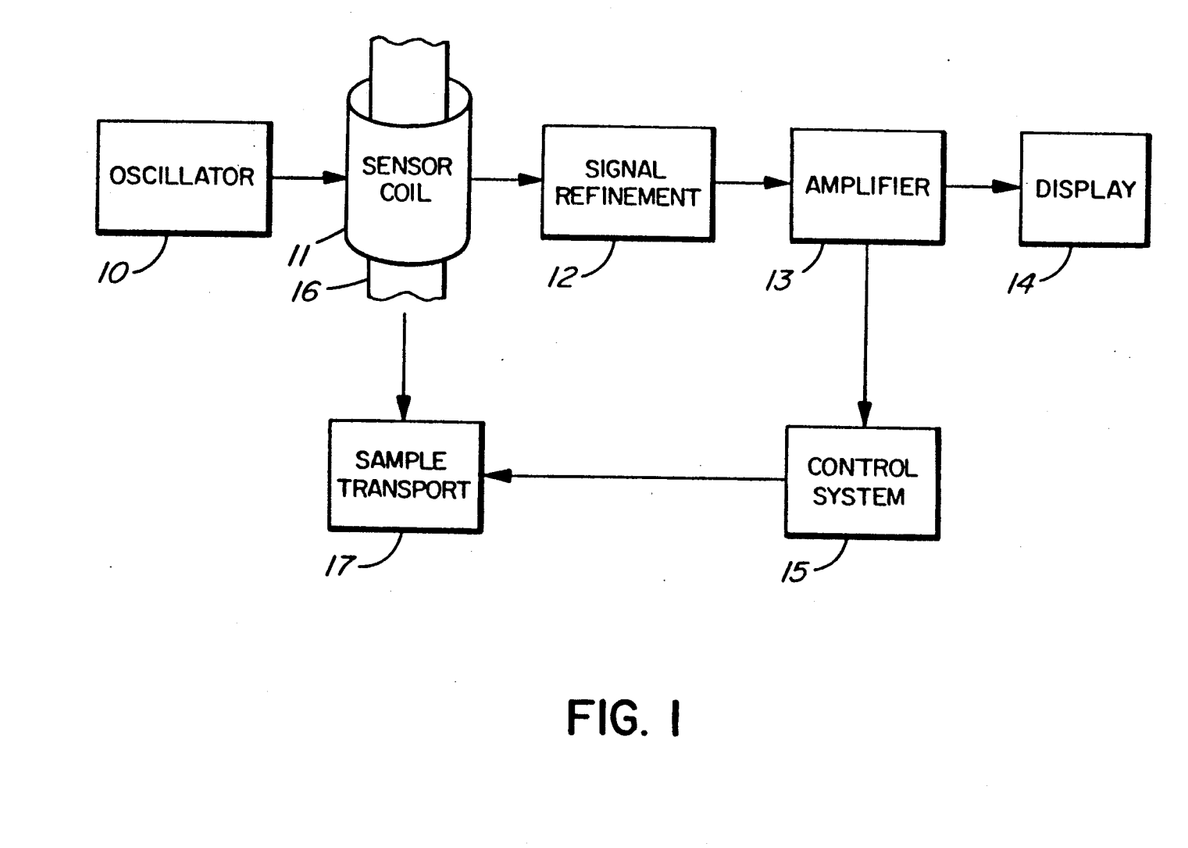
FIG. 1 is an algorithm illustrating an overall block diagram in an on-line closed loop control implementation according to the invention.

With reference now to the drawings, the elements included in carrying out the invention are illustrated in FIG. 1. They include an oscillator circuit generally illustrated at 10, a sensor coil generally illustrated at 11, signal refinement circuitry generally illustrated at 12, an amplifier generally illustrated at 13, display circuitry generally illustrated at 14 and closed loop control circuitry generally illustrated at 15. The closed loop control circuitry 15 is used only in on-line control implementations where it varies the speed at which the sample transport generally illustrated at 17 pulls the sample 16 through the production system.

Figure 2:
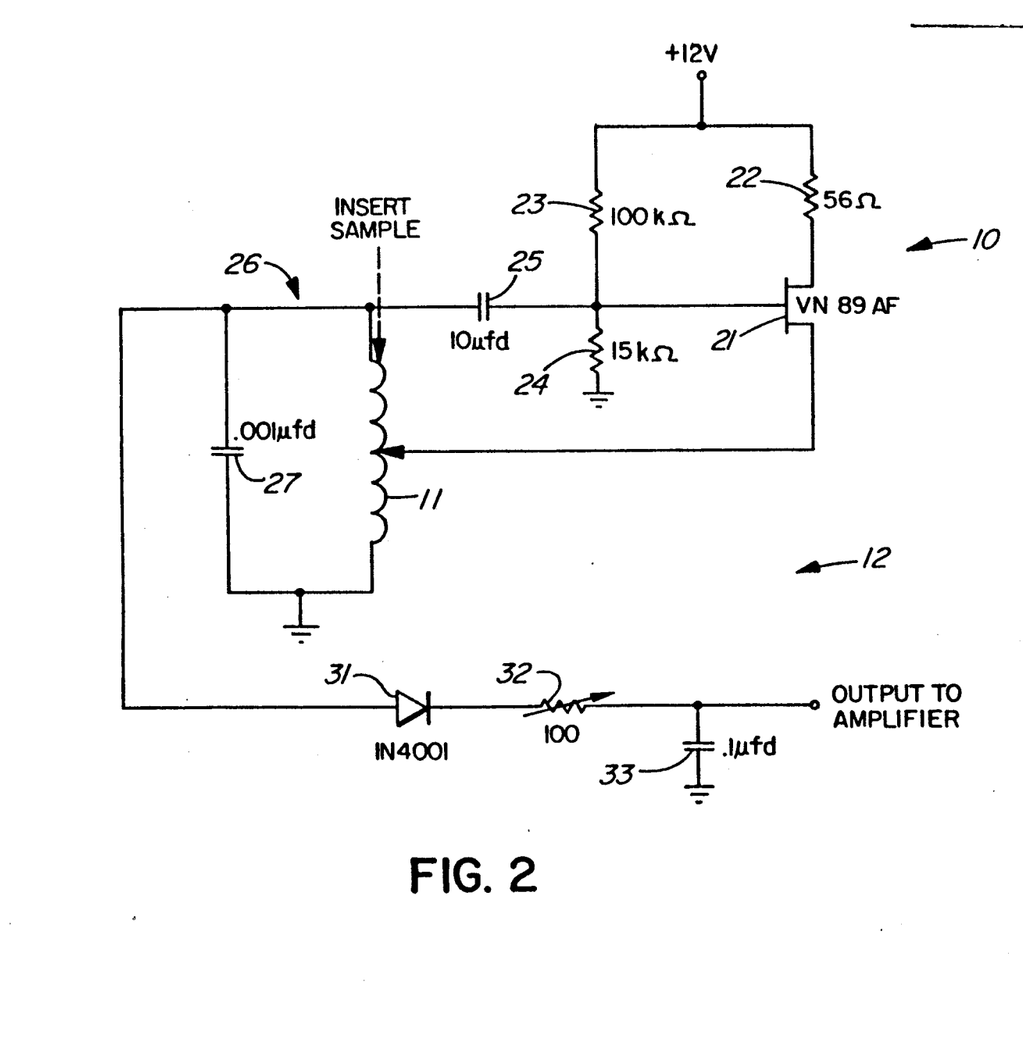
FIG. 2 is a schematic diagram of the oscillator and signal refinement circuitry of FIG. 1.

The oscillator 10 is shown in more detail in FIG. 2. It includes a field effect transistor 21, bias resistors 22, 23, 24, coupling capacitor 25 and tank circuit 26. The tank circuit 26 includes the sensor coil 11, and a capacitor 27.

The signal refinement circuitry 12 comprises diode 31, and a lowpass filter comprised of variable resistor 32 and capacitor 33.

Figure 3:
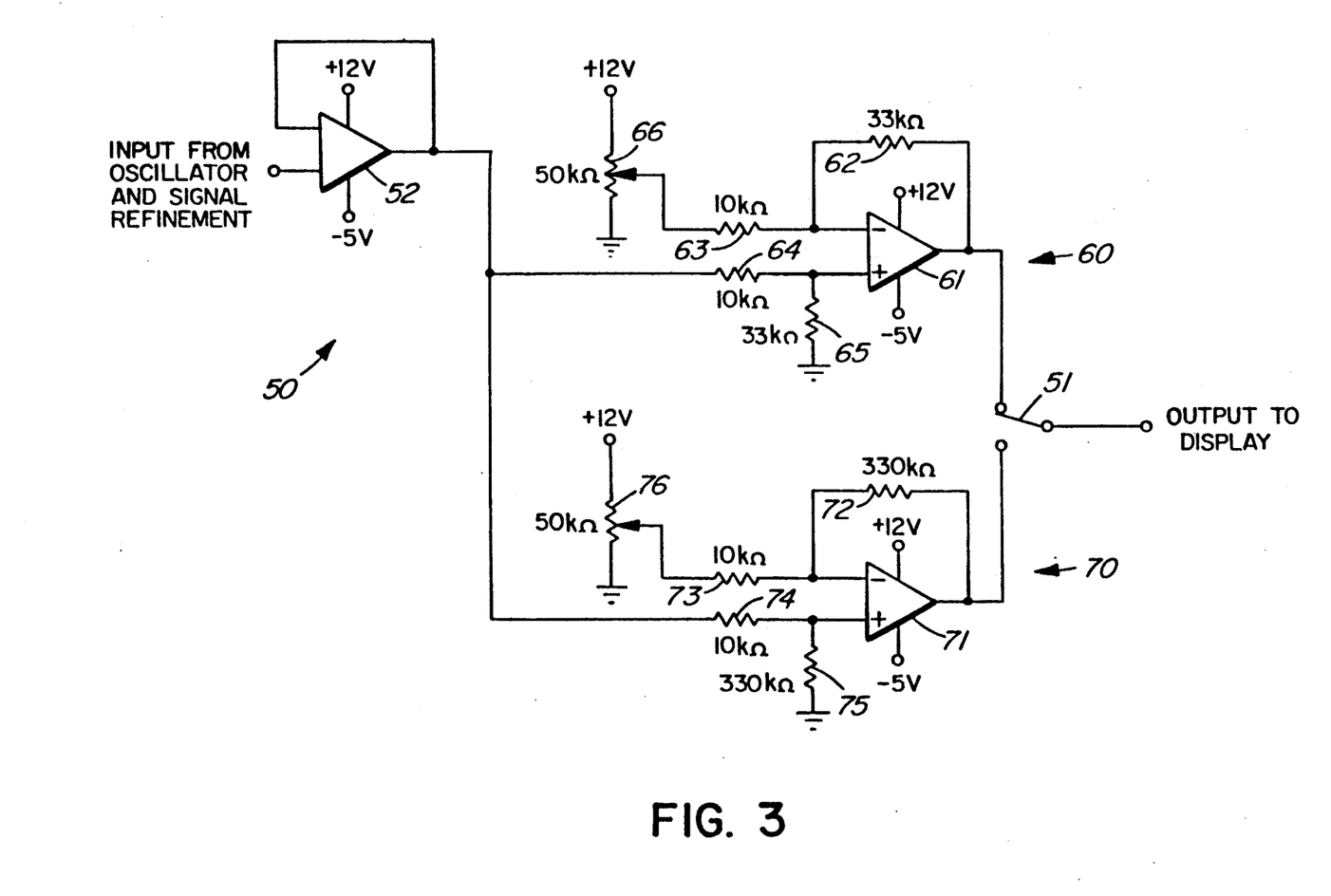
FIG. 3 is a schematic diagram of the amplifier circuitry of FIG. 1.

The components of amplifier 13 are illustrated in FIG. 3 and comprise the voltage follower stage 50 and two sample dependent output stages 60, 70, which are chosen by switch 51. The voltage follower stage 50 comprises a differential amplifier 52 with unity gain negative feedback. The output stage 60 comprises a differential amplifier 61 with gain ratio resistors 62, 63, 64, 65 and a potentiometer 66 described in more detail hereafter. Similarly, output stage 70 comprises a differential amplifier 71 with gain ratio resistors 72, 73, 74, 75 and a potentiometer 76 also to be described in more detail hereafter.

Figure 4:
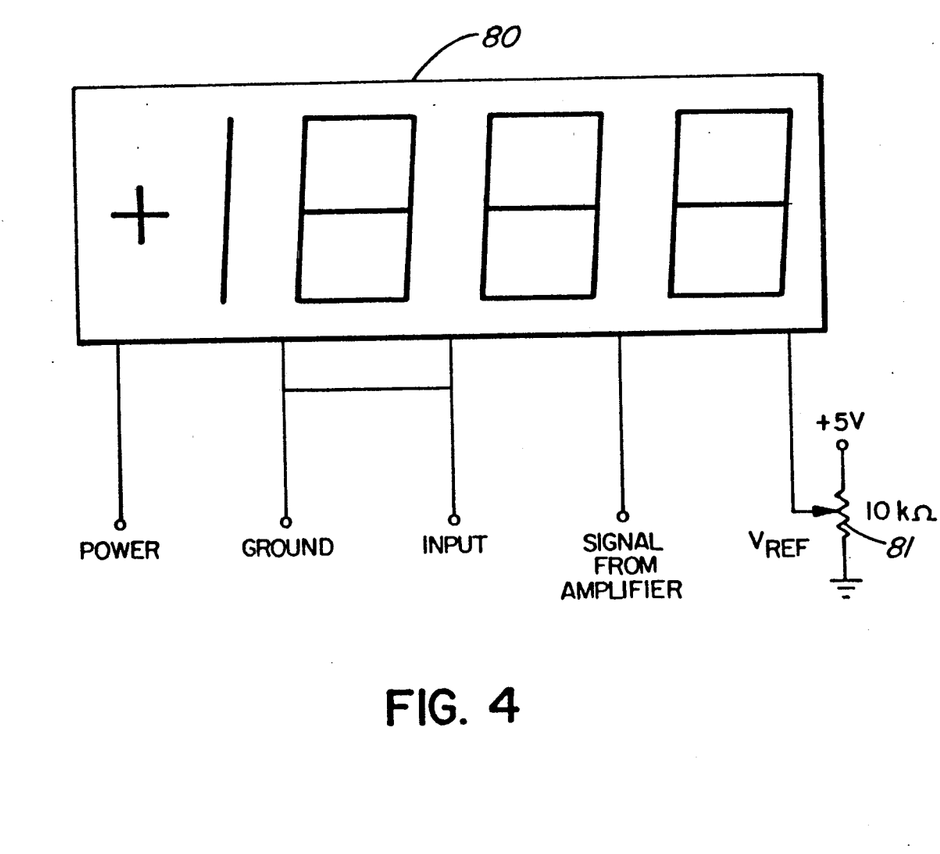
FIG. 4 is a schematic diagram of the display circuitry of FIG. 1.

The display circuitry 14 (FIG. 4.) comprises a voltage sensitive 3½ digit LED display 80 and a voltage reference created with a potentiometer 81 as will be described in more detail hereafter.

OPERATION

In operation, the properties measurable are deduced from the circuit effects attributable to changes in the resistance of the sensor coil 11 stemming from the insertion of a sample illustrated diagrammatically at 16 in FIG. 1. Two properties of the sample 16 that determine its effect on the coil resistance are its magnetic permeability $\mu$ and its electrical conductivity $\sigma$. Both of these quantities are present in skin depth equation (3) which includes the other variables "$\delta$" (skin depth) and "w" (frequency) as given below.

$$\delta = \left[ \frac{2}{\sigma \cdot \mu \cdot w} \right]^{\frac{1}{2}} \quad (3)$$

Both magnetic permeability $\mu$ and electrical conductivity $\sigma$ are also present in coil resistance relationships. The relationship describing the case of a homogeneous sample is given as equation (4) below where "a" is the radius of the sample, "1" is the length of the coil, and "N" is the number of turns in the coil. The heterogeneous equations are similar but include additional terms for the extra permeabilities and conductivities present in the sample.

$$R_{COIL \, \& \, SAMPLE \, CORE} = \left[ \frac{2 \cdot \pi \cdot a \cdot N \cdot N}{1 \cdot \delta \cdot \sigma} \right]; \quad (4)$$

$$7 \text{ kHz} < f < 5 \text{ MHz}$$

In the specific embodiment described, the oscillator 10 drives the tank circuit 26, which includes the sensor coil 11, at or very close to its resonant frequency, which is a high frequency, with no sample in the sensor coil 11. High frequency is generally considered to begin at approximately 1 MHz. This signal is half-wave rectified by diode 31 and the magnitude of the signal is adjusted with variable resistor 32. The lowpass filter of resistor 32 and capacitor 33 filter out the A.C. portion of the signal to produce an average D.C. value. This signal is then amplified by amplifier 13 and directed to display 14. The potentiometers 66, 76, 81 are used to optimize circuit response for a range of samples, set a zero reference and set a calibration scale.

When a metallic sample 16 such as a coated wire is inserted into the sensor coil 11, the resistance presented by the tank circuit 26 increases and the output signal voltage decreases. Thus the output signal reduces as more sample is added to the coil core 16. This result is indicated by the LED display 80 in display circuitry 14.

The actual property sought can be deduced from tables or graphs generated from experiments on a set of standard samples, or from a microprocessor with the same datum stored and being recalled as desired. Such a graph would be similar to that shown in FIG. 7.

Figure 5:
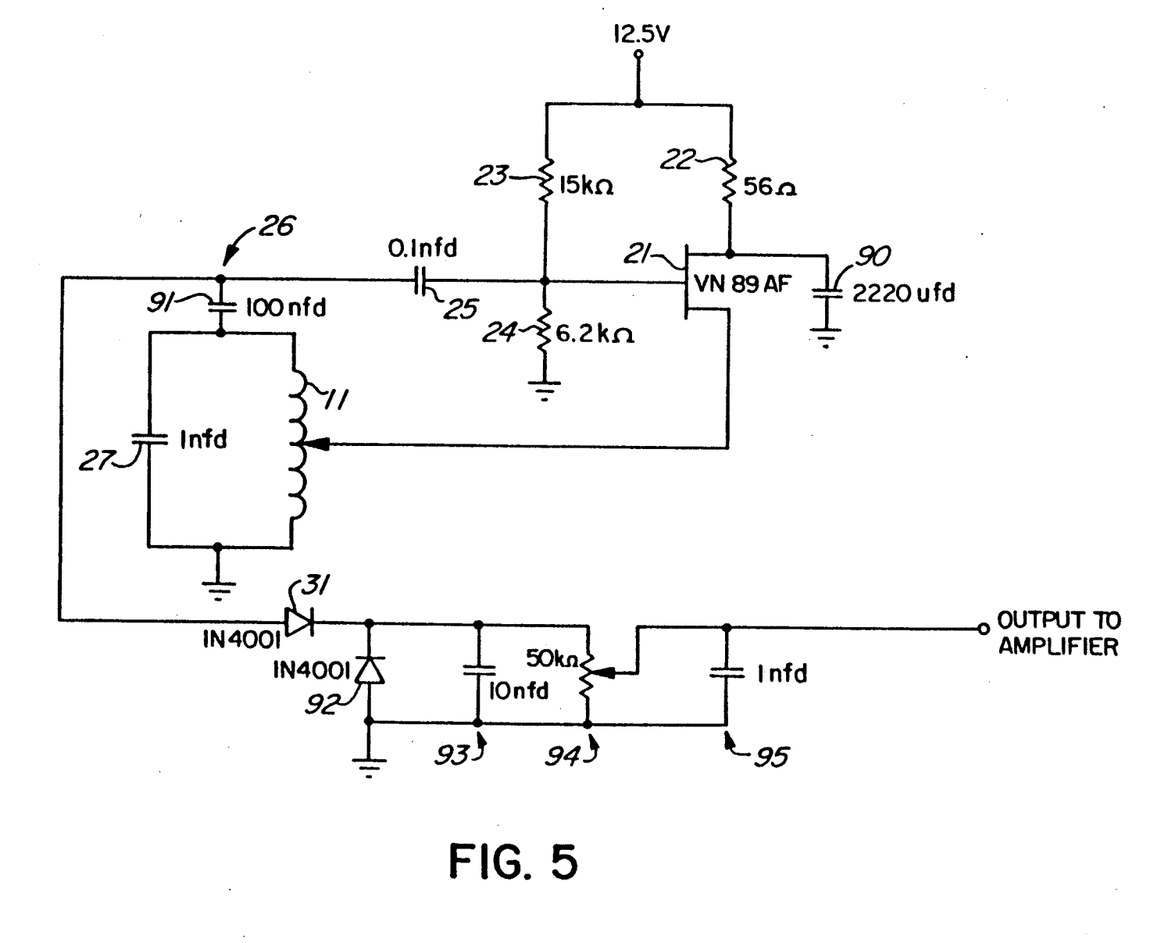
FIG. 5 is a schematic diagram of an alternative embodiment of the oscillator and signal refinement circuitry.
Figure 6:
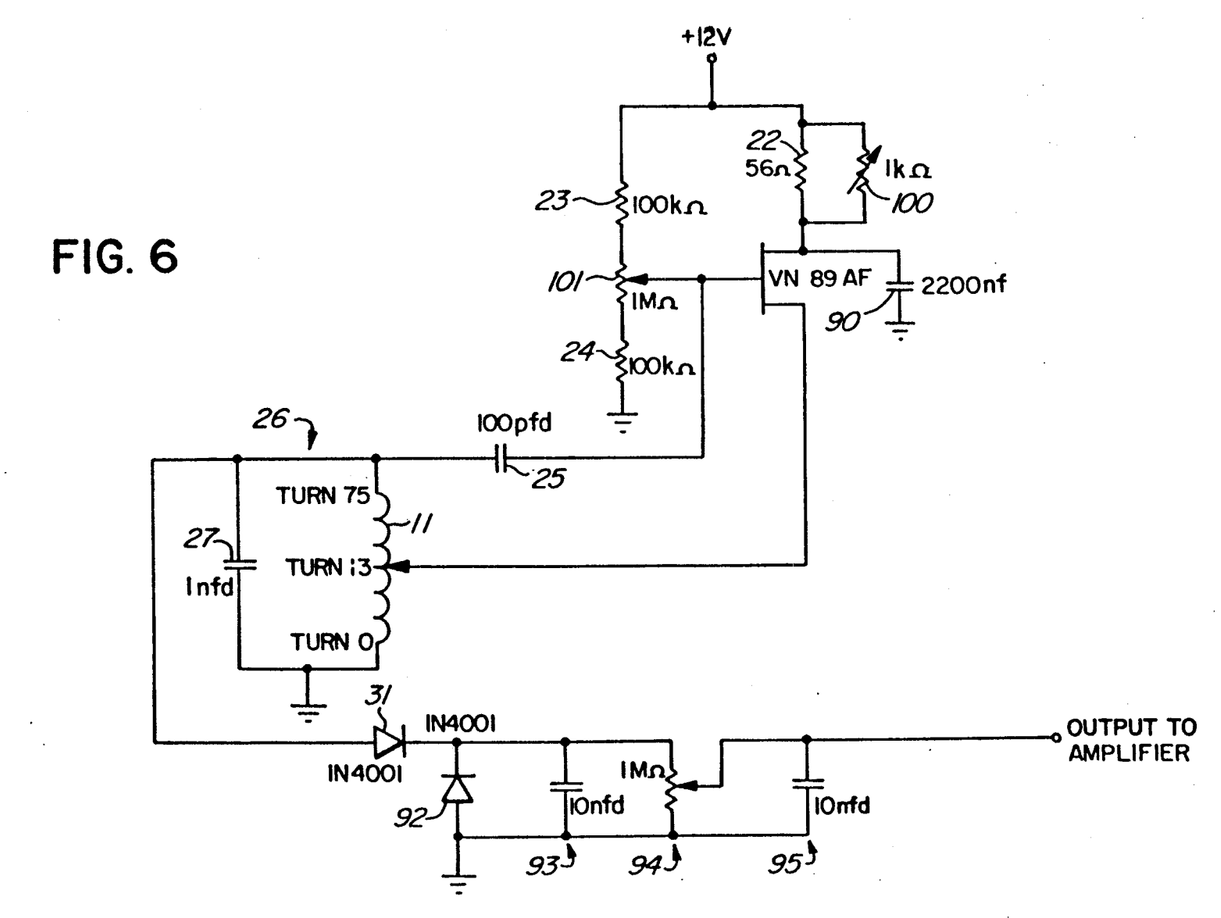
FIG. 6 is a schematic diagram of a further embodiment of the oscillator and signal refinement circuitry.

Two further embodiments of the oscillator circuitry 10 and the signal refinement circuitry 12 are available as illustrated in FIGS. 5 and 6.

The FIG. 5 embodiment differs from that described in FIG. 2 in three ways. First, coil 11, biasing resistors 23, 24, and coupling capacitor 25 have been changed in value. Second, variable resistor 32 and capacitor 33 of the lowpass output filter have been removed. Third, capacitor 90 has been added to the FET 21 biasing circuitry, capacitor 91 has been added to the tank circuit 26 and the output stage includes diode 92, capacitor 93, potentiometer 94 and capacitor 95.

Measurement results using this alternative circuit have improved. This is so since a longer sensor coil 11 is now used to average anomalies inherent in a galvanized coating. This change reduces longitudinal sensitivity and produces a more useful measurement for industrial purposes. By rebiasing the FET 21 and retuning the tank circuit 26, higher signal voltage swings have been produced, increasing instrument sensitivity. A new output lowpass filter has been added with a diode 92 placed so as to prevent the grounding of the output signal at high frequencies.

The FIG. 6 embodiment differs from the circuit of FIG. 5 in three principal ways. First, coil 11, biasing resistors 23, 24, coupling capacitor 25, potentiometer 94 and output capacitor 95 have been changed in value. Second, tank circuit capacitor 91 has been removed. Third, variable resistor 100 and potentiometer 101 have been added to the FET 21 biasing circuitry.

This circuit also shows improvement in both performance and production. In terms of performance, the circuit has been rebiased and retuned to slightly increase sensitivity. Resistor 94 has been substantially increased to prevent signal loading. In terms of production, more variable resistors have been added to overcome low component tolerances. In this way, production instruments can be easily calibrated to high standards of accuracy and precision.

Figure 7:
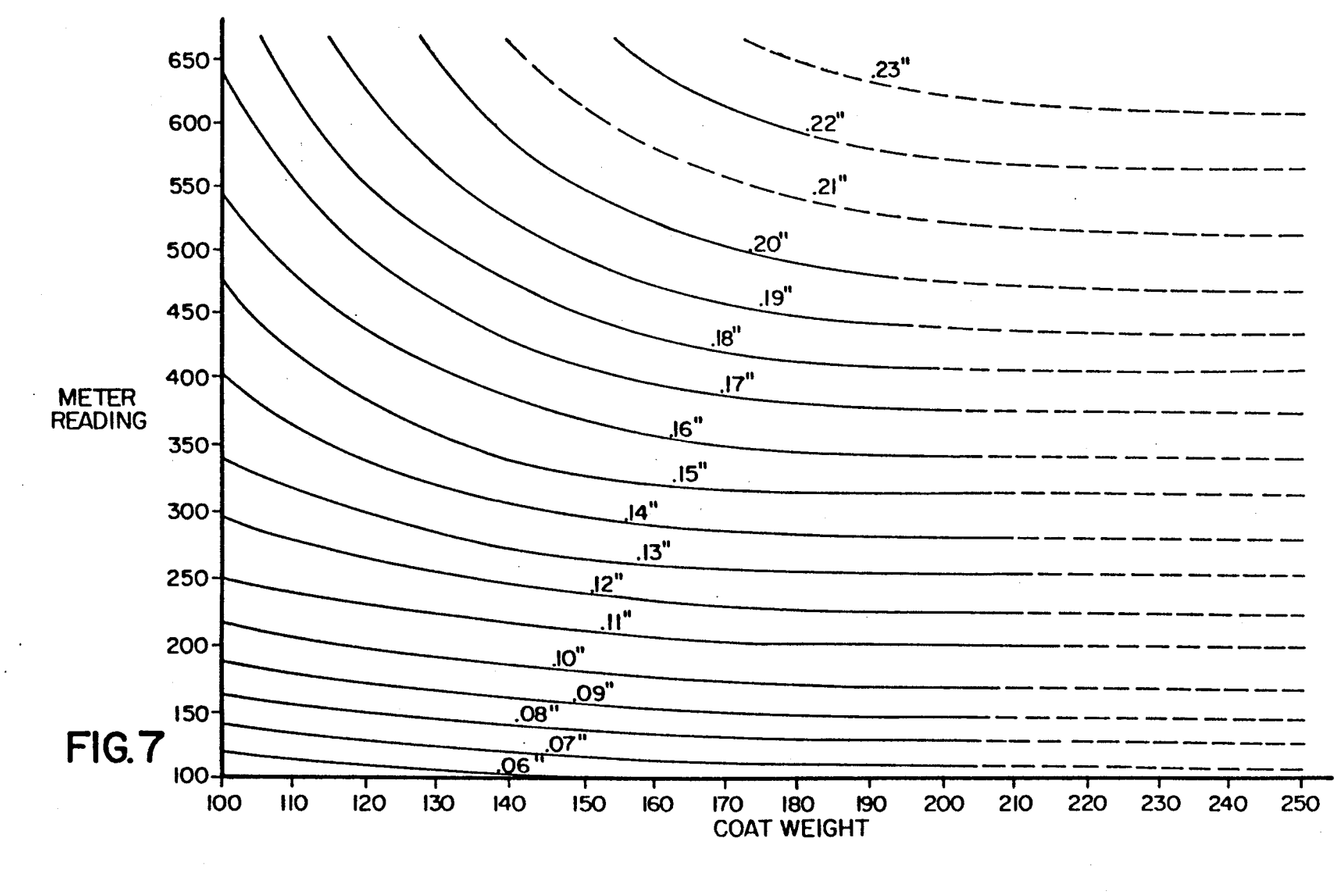
FIG. 7 is a family of curves relating the amount of zinc galvanizing coating on particular diameters of bare steel wire to the digital display of the invention in test results according to a specific embodiment of the invention.

In operations to date, extensive testing has been carried out to develop families of curves relating the amount of zinc galvanizing coating on a bare steel wire to a corresponding reading on the LED display 80. FIG. 7 is a result. Each curve in FIG. 7 represents a bare steel wire of a particular diameter that is subjected to differing amounts of galvanizing. The x-axis represents the zinc coat weight per unit surface area of substrate and the y-axis represents the unitless reading of LED display 80.

These curves were developed after plotting data points with a resonant frequency for the coil and associated capacitance being approximately 3 MHz and applying a high frequency of approximately 3 MHz to the coil. For example, a sample datum was measured as follows. The instrument was zeroed with no sample inserted into a two inch long, twenty turn sensor coil. A galvanized steel wire having a bare diameter of 0.0630" was then inserted into the coil. The LED display 80 indicated 107. Subsequent gravimetric testing reported that the coat weight of the sample was 1.29 oz/sq ft. Thus this datum was a member of the set of data points with bare steel wire diameter equal to 0.0630' and its particular coordinates were (107, 1.29).

This invention is easily applied to the measurement of other metallic coatings. Uses envisioned include measurement of the amount of aluminum or chromium coating on a steel substrate.

Other uses are available according to the invention for rapid nondestructive electromagnetic testing techniques in metals besides measuring the amount of the galvanic coating of wire. For example, producers of aluminum or copper products might apply electromagnetic testing to measure thicknesses and diameters with coils instead of having to take samples off-line to use mechanical micrometer techniques or incorporating the use of an on-line laser micrometer system. As a method for detecting the grade of an alloy, electromagnetic testing could be used in place of chemical testing. The method could also find application in the detection of flaws in the production of metals.

In maintenance and testing applications, it is contemplated that a portable version could be taken into the field to measure the dimensions set out instead of relying upon a micrometer. It also might find use in testing for flaws other than in the production of metals. For example, it is important for the safe operation of elevators, ski-lifts, and cranes that their cables not have broken strands. It is contemplated that the measurement technique according to the invention could be an alternative to the use of bulky X-ray equipment in locating broken internal strands in a cable.

It is also contemplated that it may be possible to utilize the teaching of the invention without actual insertion of the sample into the coil. For example, a high frequency at approximately the resonant frequency of the coil and associated capacitance would be applied to obtain a datum for impedance measurement. A known sample of a metallic material could then be brought into proximity to the coil and the impedance change could be recorded. Further samples would then cause impedance changes which, again, could be calibrated to determine the precise metallic characteristics of the unknown samples. The proximity would of course be equal for all samples.

While a specific embodiment of the invention has been described, many modifications to the invention will readily occur to those skilled in the art and the description herein should be taken as illustrative of the invention only and not as limiting its scope as defined in accordance with the accompanying claims.

What is claimed is:

1. A method of determining the thickness of a coating on a coated metallic substrate comprising the steps of applying a high A.C. frequency of greater than 1 MHz to a coil, said high A.C. frequency being approximately the same as the resonant frequency of said coil and its associated tank circuit, inserting said coated substrate into said coil and measuring the impedance change of said coil upon insertion of said coated substrate.

2. A method as in claim 1 wherein said coating is metallic.

3. A method as in claim 2 wherein said coated substrate is steel and said coating is zinc.

4. A method as in claim 3 wherein said coated substrate is moved through said coil and said impedance change is measured while said coated substrate is moving through said coil.

5. A method as in claim 3 wherein said coated substrate is stationary relative to said coil when said impedance change is measured.

6. A method as in claim 3 wherein said frequency applied to said coil and said resonant frequency of said coil and associated capacitance is approximately three (3) MHz.

7. A method as in claim 2 wherein said high frequency is above one (1) MHz.

8. Apparatus for determining the thickness of the coating of a coated substrate comprising a coil, a tank circuit associated with said coil, said coil and said tank circuit having a resonant frequency, a frequency generating means to generate a high A.C. frequency of greater than 1 MHz at approximately the same frequency as said resonant frequency of said coil and tank circuit, and impedance change measuring means operable to measure the change in impedance of said coil and said tank circuit when said coated substrate is inserted into said coil.

9. Apparatus as in claim 8 wherein said resonant frequency of said coil and tank circuit and said high frequency applied to said coil is between 1 MHz and 5 MHz.

10. A method of measuring the change in impedance of a coil when a coated metallic substrate is inserted into said coil comprising measuring the impedance of said coil without said coated metallic substrate being within said coil, inserting said coated metallic substrate into said coil applying a high A.C. frequency to said coil of greater than 1 MHz and at approximately the resonant frequency of said coil and tank circuit and measuring the change in impedance of said coil with said metallic substrate material within said coil.

* * * * *